United States Patent [19]

Kashiuchi et al.

[11] 4,272,718
[45] Jun. 9, 1981

[54] MOISTURE METER

[75] Inventors: Yoshinobu Kashiuchi; Isamu Zinguzi, both of Osaka, Japan

[73] Assignee: Sumitomo Electric Industries, Ltd., Osaka, Japan

[21] Appl. No.: 43,645

[22] Filed: May 30, 1979

[30] Foreign Application Priority Data

Nov. 30, 1977 [JP] Japan .................. 52-143557
Feb. 28, 1978 [JP] Japan .................. 53-23073

[51] Int. Cl.³ .......................... G01R 27/26
[52] U.S. Cl. .................. 324/61 R; 324/60 C; 324/61 QL
[58] Field of Search ............ 324/61 R, 61 P, 60 R, 324/60 C, 61 QS, 61 QL

[56] References Cited

U.S. PATENT DOCUMENTS 3,095,535  6/1963  Jaffe et al. ............... 324/438
3,684,953  8/1972  Grant ...................... 324/61 R Primary Examiner—Ernest F. Karlsen
Attorney, Agent, or Firm—Wenderoth, Lind & Ponack

[57] ABSTRACT

A moisture meter of an electrostatic type includes resonance circuits, a measuring electrode connected in parallel with the resonance circuits for measuring the capacitance of a sample, and a variable capacitance diode controlled in accordance with the capacitance across the electrode.

4 Claims, 6 Drawing Figures

MOISTURE METER

BACKGROUND OF THE INVENTION

The present invention relates to a moisture meter. More particularly, it relates to an electrostatic type moisture meter having a resonant or resonance circuit, and a measuring electrode connected in parallel therewith, said resonance circuit including a variable capacitance element. The moisture meter takes a precise measurement of an increase in capacitance across the electrode, and hence measures the water content in accordance with the increase in capacitance of the variable capacitance element.

Since the water content of a sample is proportional to the capacitance thereof, a measurement of the latter provides the water content therein, as is known. Thus, among the conventional moisture meters, a typical meter has a resonance circuit and a measuring electrode connected in parallel therewith and having a sample such as sand, between the electrodes, the capacitance of the sample is found through the measurement of the change in capacitance of the resonance circuit, thus permitting the measurement of the water content in the sample based on the linearity between the capacitance and the water content.

However, the moisture meter of this type has disadvantages in some respects. For example, since a bridge circuit is most widely used to find the change in capacitance across the electrode in the conventional moisture meter, an unbalanced bridge output voltage is phase-detected to remove any influence of a resistance involved therein, thus finding an output in proportion to the change in capacitance. When the resistance varies in a small range, it has only a negligible influence upon the precise measurement of the capacitance, but when the resistance varies in a wide range, the influence due to the resistance is not negligible. Then, a measurement without the influence of the resistance may be conducted by connecting the electrode in parallel with the resonance circuit having a variable capacitance element, and replacing the change in capacitance across the electrodes with the change in capacitance in the variable capacitance element. A variable capacitor is most readily used as a variable capacitance element in the resonance circuit. The use of the variable capacitor has in fact an advantage of accuracy in measurement of the change in the capacitance. However, as is apparent, the variable capacitor has to be operated by hand only with inconvenience or by a servomotor which will inevitably make the apparatus larger and more expensive.

Furthermore, the conventional moisture meter has a coaxial cable for connecting the electrode with the main portion of the moisture meter. The capacitance of the cable greatly varies with the change in ambient temperature, thus resulting in a large temperature drift of the resonance circuit inclusive of the cable. This drift is further accompanied by drifts in other elements such as inductance and capacitance due to the change in ambient temperature. Thus, as is apparent, a great difficulty is encountered with in the measurement of only the change in capacitance corresponding to the water content in the sample between the electrodes. In addition, so far as the electrode is connected with the main portion of the moisture meter with the coaxial cable, a plurality of meters are needed to measure the water content at a plurality of points.

SUMMARY OF THE INVENTION

It is, therefore, an object of the present invention to provide an improved moisture meter comprising a resonance circuit having a variable capacitance diode as a capacitance element, and a measuring electrode connected in parallel with the resonance circuit so that the change in capacitance across the electrode is replaced with the change in capacitance of the diode, and the change is converted into a voltage and thus the water content. The moisture meter of this invention further includes a second variable capacitance diode as a capacitance component in a CR oscillation circuit. To the first and the second variable capacitance diodes, the same reverse voltage are applied so as to make the capacitance thereof equivalent in value. Thus, the change in capacitance across the electrode is replaced with the change in capacitance across the first diode so that the second diode will develop a change in width of pulses as an output of the CR oscillation circuit in accordance with the change in capacitance in the resonance circuit. The pulse width is then converted into an output voltage which represents the water content of the sample under examination.

It is also an object of the invention to provide a moisture meter having an improved long-term stability in the measurement by correcting automatically the drift of the resonance circuit due to the change in ambient temperature.

It is a further object of the present invention to provide a moisture meter which is so adapted that a single main portion thereof can be used with a plurality of the electrodes.

BRIEF DESCRIPTION OF THE DRAWINGS

Other features and objects of the present invention will be apparent from the following description of preferred embodiments thereof with reference to the attached drawings, in which.

DESCRIPTION OF THE PREFERRED EMBODIMENTS

Figure 1:
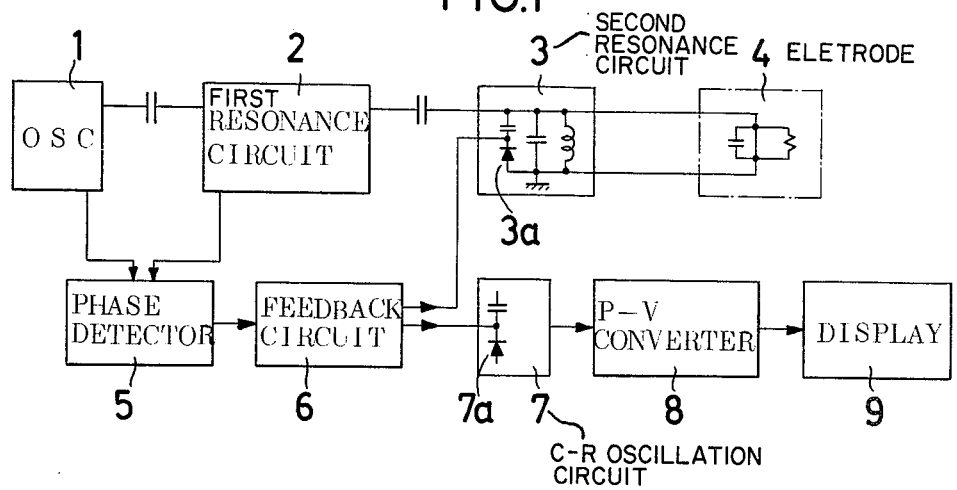
FIG. 1 is a block diagram of a circuit used in an embodiment of the invention.

Referring first to FIG. 1, there is shown a resonance circuit which comprises a high frequency oscillator 1, a first resonance circuit 2 and a second resonance circuit 3 in capacitive coupling to the oscillator and in resonance. The second resonance circuit has a variable capacitance diode 3a as a capacitance component therefor, and a measuring electrode 4 is connected in parallel therewith so as to cause a drift of resonance in the second resonance circuit in accordance with an increase, Cx, in capacitance across the electrodes. This drift in turn causes a drift of the resonance in the first resonance circuit, and then a change in the phase relationship between a reference signal of the oscillator and the first resonance circuit. The detection of the change in the phase relation by a phase detector 5 causes a feedback circuit 6 connected to both the phase detector and the second resonance circuit to apply a voltage to the first variable capacitance diode 3a in the second resonance circuit so as to correct the resonance drift, thereby replacing the capacitance increment, Cx, with the corresponding increase in capacitance in the first diode. In other words, the change in the output voltage applied to the diode 3a through the feedback circuit defines the replaced change in capacitance in the diode; however, since the reverse voltage applied to the diode and the capacitance across the diode greatly vary with ambient temperature, it is practically difficult to take a precise measurement of the replaced change in capacitance across the diode based on the change in the output voltage of the feedback circuit.

According to this invention, therefore, a second variable capacitance diode 7a, similar to the first diode 3a in characteristics is provided in a CR oscillation circuit as a capacitance component therefor. The same reverse voltage is applied to both the first and the second diodes so that they have the same capacitance thereacross. Thus, the change in capacitance across the second diode represents the capacitance increase, Cx, due to the water contained in the sample under examination. Furthermore, the width of an output pulse from the CR oscillator, which is proportional to the change in capacitance across the second diode 7a, is converted by a pulse width-voltage converter 8 to a voltage which is shown on a display device 9.

Figure 2:
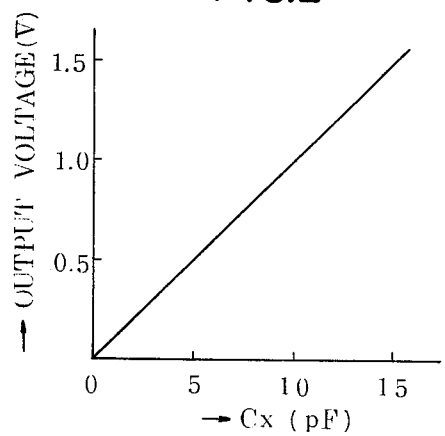
FIG. 2 is a characteristic curve illustrating the linearity between an increase in capacitance, Cx, across the electrodes due to the water content of the sample therebetween and an output voltage, V, converted therefrom through the circuit shown in FIG. 1.
Figure 3:
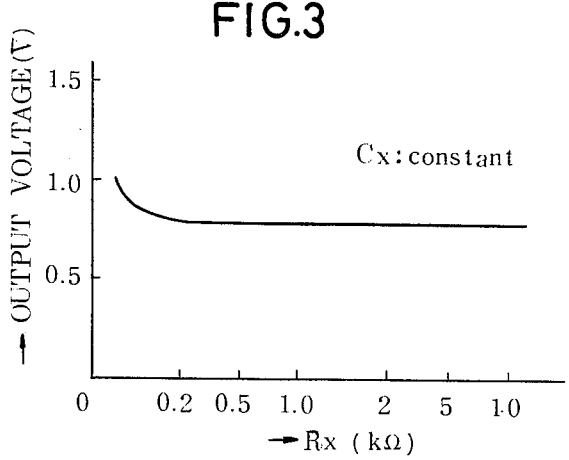
FIG. 3 is a characteristic curve illustrating the relationship between Cx and a resistance, Rx, positioned in parallel thereto.

With the moisture meter described above, the output voltage, V, is in proportion to the capacitance increase, Cx, as shown in FIG. 2. Furthermore, the resistance, Rx, connected in parallel with the electrode has no influence upon the output voltage when Rx is larger than 200 ohms, as shown in FIG. 3.

The moisture meter of the invention is so adapted as to display the output voltage digitally, and hence has an advantage in that the water content of the sample can also be digitally read directly on the display, provided that the sample has a capacitance proportional to the water content thereof.

Figure 4:
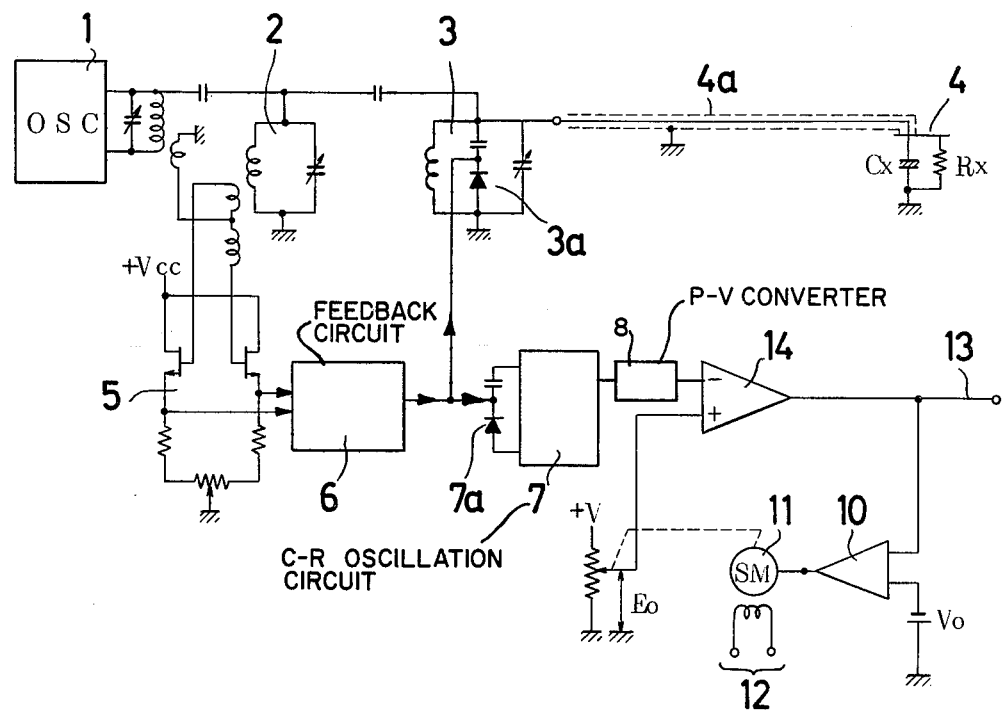
FIG. 4 is a block diagram of a circuit used in another embodiment of the invention; and, FIGS. 5 and 6 are block diagrams of circuits used in other embodiments of the invention.

FIG. 4 illustrates a block diagram of a circuit of another embodiment of the invention, in which the same reference numerals as those in FIG. 1 designate the same parts or elements, and the numerals 10, 11, 12 and 13 designate a servoamplifier, a servomotor, feedback sampling input terminals, and an output terminal, respectively. With the electrode left in the air, a differential amplifier 14 should develop an output voltage of Vo as a reference voltage. Thus, any deviation from Vo can be regarded to be due to the drift. The output voltage of the difference amplifier 14 is compared with the reference voltage Vo by the servoamplifier 10 to detect the difference therebetween. The servomotor is driven in accordance with the magnitude of the detected difference upon the application of a signal to the feedback sampling terminals 12, thereby controlling the reference voltage for the differential amplifier 14. The reference voltage is controlled to correct the drift by applying a signal to the sampling terminals 12 with no sample between the electrodes. When no signal is applied to sampling terminals 12, the servomotor 11 is locked. This makes possible a stable and accurate measurement by performing drift corrections at a desired interval of time.

Figure 5:
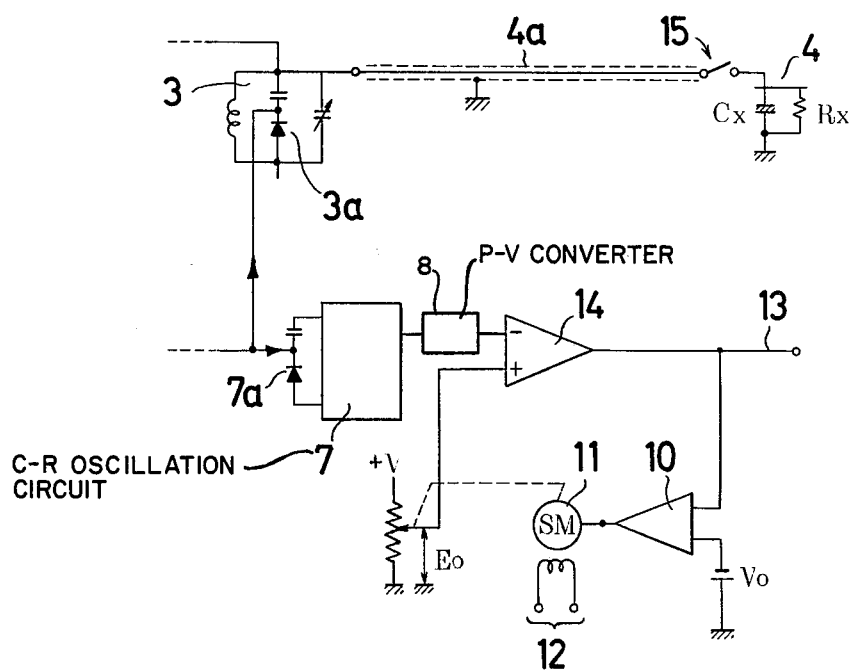

FIG. 5 illustrates a block diagram of a circuit of a further embodiment of the invention, in which a switch 15 is provided between the electrode 4 and the coaxial cable 4a. When the switch is turned off, the entire circuit will be in the same condition as when the electrode is in air. The drift correction is made by applying a signal to the sampling terminals 12 with the switch turned off. This embodiment has an advantage in that the drift correction can be carried out even during measurement. With this embodiment, the reference voltage of the difference amplifier 14 is controlled for the correction of drift either with no sample between the electrodes or with the switch 15 turned off.

In the above embodiment, the switch may be replaced with a relay, transistor or the like which can turn on and off a high-frequency signal. The reference voltage can also be controlled by a pure electronic circuit instead of the servomotor.

Figure 6:
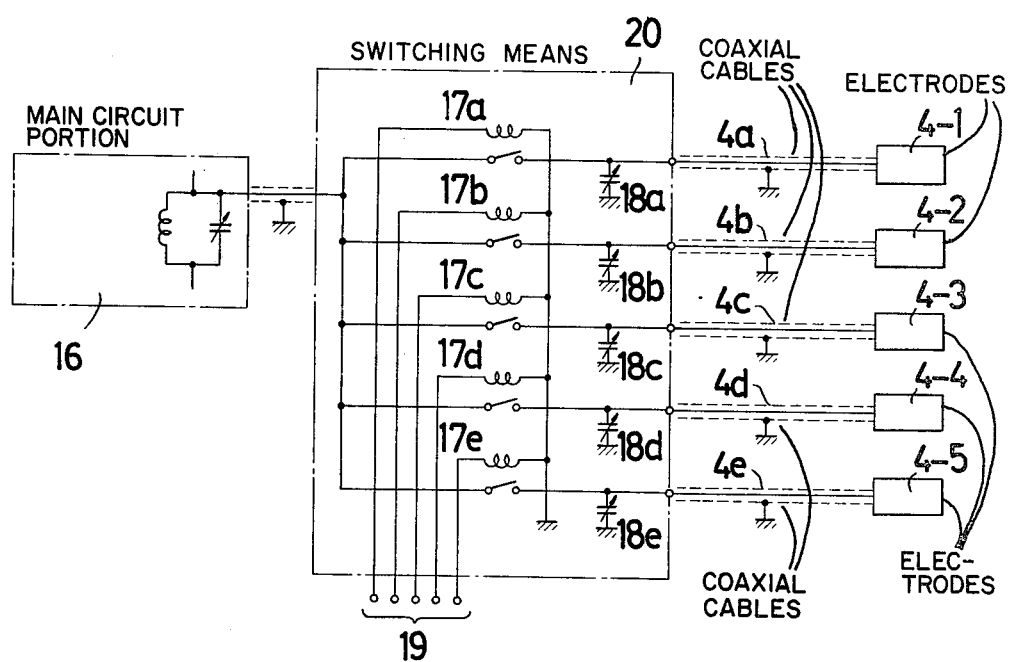

FIG. 6 shows a block diagram of a circuit used in a further embodiment of the invention, which comprises a main circuit portion 16 having a high frequency oscillator and the resonance circuits, a plurality of coaxial cables 4a through 4e, measuring electrodes 4-1 through 4-5, each connected to its respective cable, and a switching means 20. This means comprises relays 17a through 17e which have input terminals 19 connected therewith, and variable capacitance elements 18a through 18e between the cables and the relays so as to select any one of the electrodes for measurement. The switching means may comprise high frequency switching elements other than relays, if desired.

A selection signal for the selection of a specific electrode is applied to a selected input terminal 19 to operate a respective relay which in turn connects the main portion of the meter with a selected cable and thus a selected electrode. Thus, this circuit configuration permits measurement at more than one point.

Since all the coaxial cables are not the same length, the individual capacitances of the electrodes plus the coaxial cables are, in general, different from each other in relation to the main portion. Therefore, variable capacitance elements, such as variable capacitors, are provided between the relays and the cables so that all the reference capacitances will be the same. This permits the measurement under same conditions, regardless of which electrode is selected. Furthermore, the above circuit configuration ensures that the main portion, which is usually expensive, can be used in common with a plurality of electrodes, thus having an economical advantage over the conventional moisture meter.

What is claimed is:

1. A moisture meter for measuring the moisture content of a sample and comprising:
   an oscillator;
   a first resonant circuit;
   a second resonant circuit having a first variable capacitance diode;
   said first and second resonant circuits capacitively coupled to said oscillator and in resonance;
   an electrode connected in parallel with said second resonant circuit for receiving said sample to be measured;
   a phase detector connected to said oscillator and said first resonant circuit for detecting the drift in the resonant frequency point of said first resonant circuit;

a feedback circuit connected to said phase detector and said second resonant circuit to apply a voltage to said first variable capacitance diode to cancel said drift in said resonant frequency point;

an oscillation circuit for producing pulses and including a second variable capacitance diode having substantially the same characteristics as said first variable capacitance diode, said second variable capacitance diode also receiving said voltage from said feedback circuit, the pulse width of said oscillation circuit pulses having a predetermined relationship to the capacitance of said second diode; and a pulse width to voltage converter connected to said oscillation circuit for converting the width of the pulses from said oscillation circuit to an output voltage of the moisture meter; said output voltage having a predetermined relationship to the moisture content of said measured sample.

2. A moisture meter as claimed in claim 1, further comprising:

a differential amplifier for comparing the output voltage from said pulse width to voltage converter with a reference voltage and for providing an output voltage equal to the difference between said converter output voltage and said reference voltage, said amplifier output voltage having a predetermined relationship to the moisture content of said measured sample;

a servoamplifier for comparing the output voltage from said differential amplifier with a predetermined voltage and for providing a difference voltage between said amplifier output voltage and said predetermined voltage; and a servomotor driven by said difference voltage of said servoamplifier to control said reference voltage for said differential amplifier.

3. A moisture meter as claimed in claims 1 or 2, further comprising a switch disposed between said electrode and said second resonant circuit.

4. A moisture meter as claimed in claim 2, further comprising at least one additional electrode and switch, said at least one additional electrode respectively connected by its additional switch to said second resonant circuit, wherein said switch and said at least one additional switch are operated to connect one of said electrode and said at least one additional electrode to said second resonant circuit.

* * * * *